(12) United States Patent
Wilkening et al.

(10) Patent No.: US 7,544,495 B2
(45) Date of Patent: Jun. 9, 2009

(54) METHODS FOR PRODUCING ETHANOL AND METHANE FROM BIOMASS

(76) Inventors: Carl Ludwig Wilkening, Östbergweg 9, 30559 Hannover (DE); Ludz Wilkening, Im Mehlhof 20, 29351 Eldingen-Ziegelei (DE)

(*) Notice: Subject to any disclaimer, the term of this patent is extended or adjusted under 35 U.S.C. 154(b) by 6 days.

(21) Appl. No.: 10/561,249

(22) PCT Filed: Jun. 21, 2004

(86) PCT No.: PCT/EP2004/006700

§ 371 (c)(1),
(2), (4) Date: Sep. 15, 2006

(87) PCT Pub. No.: WO2004/113549

PCT Pub. Date: Dec. 29, 2004

(65) Prior Publication Data

US 2007/0190626 A1 Aug. 16, 2007

Related U.S. Application Data

(60) Provisional application No. 60/499,379, filed on Sep. 3, 2003.

(30) Foreign Application Priority Data

Jun. 20, 2003 (DE) .................. 103 27 954

(51) Int. Cl.
    *C12P 7/06* (2006.01)
(52) U.S. Cl. .................. 435/161; 435/167
(58) Field of Classification Search .................. None
    See application file for complete search history.

(56) References Cited

U.S. PATENT DOCUMENTS

5,559,031 A * 9/1996 Zinnamosca et al. ..... 435/289.1
6,355,456 B1   3/2002 Hallberg et al.

FOREIGN PATENT DOCUMENTS

WO   WO 2004/113549 A1   12/2004

OTHER PUBLICATIONS

Bryan et al: "IOWA Ethanol Plant Pre-Feasibility" [Online] 2000, XP002300947 Retrieved from the Internet: URL:http://www.iowaagopportunity.org/ethan olmanual/plant.pdf>; [retrieved on Oct. 15, 2004].*

Marnichenko V A et al: "Intensified saccharification and fermentation of starchy raw material subjected to prior mechanical/chemical destruction.",1978.*

(Continued)

*Primary Examiner*—Deborah D Carr
(74) *Attorney, Agent, or Firm*—Arnold & Porter LLP (57) ABSTRACT

The present invention relates to methods for producing ethanol and methane from biomass. The clear phase of a pulp obtained by fermentation of milled biomass is used for obtaining methane gas for energy production and for conversion in a combined heat and power production of energy and steam. The anaerobically purified clear phase of the pulp can additionally be purified aerobically to enable reuse of the water in the process. The solid phase of the pulp can be utilized for obtaining a high quality feeding stuff or burned for production of energy.

41 Claims, 3 Drawing Sheets

OTHER PUBLICATIONS

Edmond A et al: Bioresource Technology, vol. 75, No. 1, Oct. 2000, pp. 49-55.*

Wayman M et al: Starch, vol. 40, No. 11, 1988, pp. 418-422.*

Weiland P et al, Water Science and Technology, vol. 22, No. 1-2, 1990, pp. 385-394.*

Fukuzaki S et al: Journal of Fermentation and Bioengineering, vol. 79, No. 4, 1995, pp. 354-359.*

Derwent Publ. Limited, Abstract AN 1981-35285D (Jul. 10, 1931).

Database FSTA International Food Information Service Database Accession No. 79-2-11-H1802 Abstract, "Intensified saccharification of fermentation of starchy raw material subjected to prior mechanical/chemical destruction".

Bryan & Bryan Inc., "Iowa Ethanol Plant Pre-Feasibility Study", pp. 20-49 (2000) and 55 pages of attachments.

Filho et al., "Babassu Coconut Starch Liquefaction : An Industrial Scale Approach to Improve Conversion Yield", *Bioresource Technology* 75:49-55 (2000).

Fukuzaki et al., "High Rate Performance and Characterization of Granular Methanogenic Sludges in Upflow Anaerobie Sludge Blanket Reactors Fed with Various Defined Substrates", *Journal of Fermentation and Bioengineering*, 79(4):354-359 (1995).

International Search Report for PCT/EP2004/006700 completed Oct. 15, 2004.

Wayman et al., "Saccharification and Fermentation of Whole Barley Ground in the *Szego* Mill", *Starch* 40:418-422 (1988).

Weiland et al., "Operational Behaviour of an Industrial Fixed Bed Reactor for Biomethanation of Alcohol Slops from Different Crops", *Wat. Sci. Tech.* 22(1/2):385-394 (1990).

Dambroth et al., "Federal Research Institute for Agriculture: Further Development and Optimizing of an Economically Friendly and Energy Saving Ethanol Production Based on Domestic Renewable Primary Products", *Final Report*, Braunschweig 1992, pp. 84-85, 112-113, 116-118, and 173 (partial document).

English Translation of Dambroth et al., "Federal Research Institute for Agriculture: Further Development and Optimizing of an Economically Friendly and Energy Saving Ethanol Production Based on Domestic Renewable Primary Products", *Final Report*, Braunschweig 1992, pp. 84-85, 112-113, 116-118 and 173 (partial document).

B8 Barbara Elvers, Ullmann's Encyclopedia of Industrial Chemistry pp. 82-94 (5$^{th}$ ed. 1995).

* cited by examiner

METHODS FOR PRODUCING ETHANOL AND METHANE FROM BIOMASS

CROSS REFERENCE TO RELATED APPLICATIONS

This national phase application is a continuation of International Application Number PCT/EP2004/006700, filed Jun. 21, 2004, which claims priority to German application No. 103 27 954.7, filed Jun. 20, 2003, and U.S. Provisional Application No. 60/499,379, filed Sep. 3, 2003.

The present invention relates to improved methods for producing ethanol and methane from biomass.

The clear phase of a pulp obtained by fermentation of milled biomass is used for obtaining methane gas for energy production and for conversion in a combined heat and power production of energy and steam. The clear phase of the pulp can be anaerobically purified and may further be be purified aerobically. The water obtained by anaerobic and/or aerobic purification may be used for the process of producing ethanol. The solid phase of the pulp can be utilized for obtaining a high quality feeding stuff or burned for production of energy.

The production of alcohols via fermentation of biomass represents one of the oldest biotechnological methods. It is used inter alia for the production of alcoholic beverages, such as beer and wine. Similarly, the production of alcohol for industrial use by fermentation of biomass is also known for a long time. The respective alcohols, in particular ethanol, are presently used as starting material for the preparation of pharmaceutical compositions, cosmetics and a number of chemicals.

Likewise, the use of ethanol obtained by fermentation as an energy carrier is known for a long time. However, due to the high costs in comparison to the exploitation of crude oil, it was not commercially employed in the past.

On account of the reduced availability of crude oil reserves and the $CO_2$-reduction requested in the Kyoto-Treaty, the possible use of bioethanol as an energy carrier attracts new interests. Consequently, there is a need for improved methods for the production of ethanol from biomass in large scale.

Several processes for the production of alcohol from biomass are described in the state of the art. Since entirely different biomasses are used as starting materials in these processes, inter alia sugarcane, sugar beet, grain etc., the processes for obtaining bioalcohols also differ from each other. Although identical starting materials may be used, different protocols for carrying out the process exist.

The fermentation processes for producing ethanol from grain all comprise
(a) reducing the size of the grain;
(b) adding microorganisms to the biomass and carrying out a fermentation; and
(c) separating the ethanol from the biomass.

The separation of the ethanol is usually achieved by distillation. In this step pulp is obtained as a side product and is usually concentrated and used as fertilizer or (after drying) as a protein-containing feeding stuff.

Each of these steps is described in many different embodiments in the state of the art. The process presently used in the art at is described for example in DE 30 07 138. This document discloses a process for the production of ethanol by fermentation of a carbohydrate-containing substrate in one or more fermentation vessels. After fermentation, the fermentation fluid is distilled, rectified, and—if necessary—dehydrated to water-free alcohol. The state of the art further teaches to split the flow of fermentation fluid in at least one flow of yeast concentrate and one yeast-free flow. The yeast concentrate flow is re-circulated into the fermentation vessel and the yeast-free phase is divided into an ethanol-rich flow and a rest flow (pulp) by means of distillation. The rest flow is partially re-circulated into the fermentation vessel. The advantage of the process described in DE 30 07 138 resides in the fact that the yeast-free flow can be processed in a simple evaporator using one or a few distillation steps, by dividing the yeast-free flow into an ethanol-rich first steam flow and a first fluid bottom flow. The steam flow is transferred into a production plant for producing the desired ethanol quality. The bottom flow is partially re-circulated into the fermenter, while another part is lead to a depression unit, wherein this part is divided into an ethanol-rich second steam flow and a second fluid bottom flow, which has a low concentration of ethanol.

The ethanol-rich steam flow can be used together with the first ethanol-rich steam flow for obtaining ethanol, for example in a rectification column.

Since the pulp contains large amounts of proteins, it is usually used as feeding stuff. However, the production of feeding stuff and in particular the drying of the pulp requires a lot of energy, approximately 50% of the energy needed for the entire bioethanol production process.

Furthermore, methane gas can be obtained from the pulp and the rest can be used as a fertilizer. For example, ZA80/5297 discloses a process in which ethanol is obtained from maize and the pulp is used for producing methane. For this purpose, the maize is reduced in size, bran and proteins are separated, and a substrate for fermentation is obtained. The device used for reducing the size of the corn, a swing-hammermill, usually generates fragments of comparatively large size with a particle size of approximately 2 mm. The pulp generated by fermentation and distillation is to be used for obtaining methane gas.

All processes known in the art share the problem that a long retention time is required for the purification of the clear phase. As a result, the whole production plant will become expensive since a very large volume is required. It was therefore not possible to construct bioethanol production plants producing more than 100 $m^3$ ethanol per day which obtain methane from the pulp for energy production.

The problem addressed by the invention is to provide improved methods for the production of ethanol and methane from biomass, specifically enabling a process with improved energy-efficiency.

This problem is solved by the subject matter of the claims. The invention relates to a method for producing ethanol and methane from biomass, comprising:
 a) enzymatically liquefying and saccharifying flour of a biomass with a particle size of less than 1 mm in a conventional manner in the presence of water, thereby obtaining a mash;
 b) fermenting and distilling the substrate in a conventional manner, thereby obtaining ethanol and a pulp;
 c) separating the pulp into a solid phase and a clear phase, wherein a clear phase with a content of solids of less than 1% is obtained;
 d) obtaining methane from the clear phase in a methane reactor.

To obtain the flour, biomass is milled to a particle size of less than 1 mm. Hull components, which might be present, can be substantially separated prior to step a or b, i.e. prior to liquefying and saccharifying or fermenting. In the context of this invention, biomass is defined as a complex, renewable raw material derived from plants, in particular grain. A defined or synthetic medium comprising a mixture of purified compounds is preferably not considered to fall within the term biomass or substrate as used in the present application.

According to the invention, the process has particular advantages when used for producing ethanol starting from grain as biomass. In particular, wheat, rye, maize or triticales are used. The use of wheat is especially preferred. After milling or grinding the grain, the bran should be separated. A sieve arrangement is suitable, which may also be used to determine the size of the flour particles.

Milling of the biomass, in particular the grain, can be carried out using various mills. Milling with wheat mills, rotary mills or the use of flour ground with wheat mills or rotary mills, however, is particularly preferred. Conventional methods of grinding in impact crusher- or swing hammer-mills yield a less suitable flour containing mostly particles with a size of about 2 mm and a high residual content of bran of still about 10%. Preferably, the particle size of the flour should be smaller than 1 mm or 0,6 mm, most preferred smaller than 0,5 mm or 0,2 mm. Preferably, the residual percentage of bran is less than 10%, in particular less than 5% or less than 1%. Milling of the biomass is not per se a step of the method of the present invention.

However, in the method of the present invention, a biomass of small particle size (flour) that is already partially purified, e.g., starch can also be used.

In the method of the invention, proteins present in the biomass are substantially separated from the flour prior to step a or separated from the mash prior to step b or separated from the clear phase of the pulp in step c. Separation of proteins prior to liquefaction and saccharifycation is known in the state of the art and and is used, e.g., for producing starch that is essentially free from protein. In another embodiment of the method, the proteins are separated prior to step b by precipitating the proteins present in the mash and separating them.

The clear phase of the pulp that is used for methane production has a content of solids of less than 1%, preferably a content of solid particles of less than 0,5%. The content of solids refers, if not otherwise mentioned, to volume percentages (v/v %), and can easily be determined by sedimentation. Alternatively, a centrifugation for separating solid and liquid components can be carried out. After separation, the content of solids can also be provided as weight percentage (w/v %).

In a further alternative the present invention provides processes for the production of ethanol from biomass comprising:

(a) reducing the size of the biomass to a particle size of less than 1 mm;

(b) using the biomass as a medium for fermentation; and (c) obtaining the ethanol;

wherein proteins present in the biomass and the bran optionally present are substantially separated prior to step (b) or (c).

According to the invention, it was surprisingly shown that carrying out the fermentation and/or the distillation using a substrate which was reduced to a particularly small particle size and does not contain bran or proteins of the biomass has considerable advantages in the subsequent distillation and processing. The lower content of solids and the smaller size of the remaining content of solids in the alcoholic mash results in advantages during distillation and considerable savings in energy and time in processing the pulp after distillation. The pulp with a reduced content of solid matter is particularly suitable for obtaining methane. In particular, the retention time of the cleared pulp in the methane production plant is considerably reduced when compared to the retention time of common pulp, which allows a considerable reduction of the size of the plant.

According to a preferred embodiment of the invention, a method for producing ethanol and methane from grain is provided, comprising a) milling the grain to a particle size of less than 1 mm and separating the bran from the flour;

b) enzymatically liquefying and sacchariyfing the flour in a conventional manner in the presence of water, thereby obtaining a mash;

c) substantially precipitating the proteins present in the mash by cooling, sieving and drying, thereby obtaining the proteins and a substrate;

d) fermenting and distilling the substrate in a conventional manner, thereby obtaining ethanol and pulp;

e) separating the pulp into a solid phase and a clear phase, wherein a clear phase with a content of solids of less than 1% is obtained; and f) obtaining methane from the clear phase in a high-performance methane reactor.

In a particularly preferred embodiment of the method of the invention, the proteins are only separated in step c by precipitating the proteins present in the pulp by cooling and separating them. This method is advantageous, as this way of proceeding, not only the proteins, but additionally further small solid particles or contaminants in the pulp can be separated at the same time. Preferably, yeast, fibers, solid substances, fat and/or proteins present in the pulp are agglomerated by cooling and sedimented prior to separation of the pulp into solid phase and clear phase. Preferably, agglomeration and sedimentation takes place in a residual time. If appropriate, further auxiliary substances for flocculation can be added.

It is preferred to utilize milled biomass in the method of the invention as a starting material and also for fermentation that comprises a substantial percentage of proteins, such as more than 0,35%, more than 1% or more than 5 or 8%. The clear phase of the pulp obtained upon separation of proteins in step c has an especially low content of solids, making the clear phase especially suited for methanisation, in particular methanisation in high-performance reactors.

The methane produced by the methanisation can advantageously be used for the generation of energy and/or heat that can be utilized for the process (distillation, rectification and/or drying of the solid phase of the pulp).

The feeding stuff obtainable from the protein, the bran and the solids of the pulp by the process of the invention is of a higher quality compared to feeding stuff produced by methods conventional in the art, since the feeding stuff of the invention has only been exposed to a mild heat treatment.

In the following, the individual process steps illustrated in detail:

First, the size of the biomass is reduced. For this purpose, any process for reducing the size of biomasses can be used. Numerous such processes are known in the state of the art. In particular, the size of the biomass can be reduced by milling. Reducing the size of the biomass to a granule size of less than 1 mm is preferred, wherein reducing to a particle size of less than 0,6 mm, less than 0,5 mm or to approximately 0,2 mm is particularly preferred. According to the invention, the particle size can be selected by methods known in the art, for example by sieves.

Prior or subsequent to the size reduction, the biomass can be subjected to swelling by the addition of liquid, in particular by addition of water. Preferably, the biomass is milled in a dry condition, since the bran can be separated more easily in this state. Any method known in the state of the art can be used for the separation of the bran. Usually, the bran is separated by sieves.

Subsequently, the biomass is liquefied by the addition of enzymes and saccharified, whereby a substrate is obtained. If further liquefaction is desired, water and other auxiliary agents can be additionally added.

Preferably, enzymes are employed in a higher amount than necessary in the context of the specification of activity of the enzymes, the amount of substrate and the time of saccharifycation. In particular, at least the double amount of enzyme is used to ensure complete digestion. Furthermore, the addition of cellulases is of advantage.

In the processes according to the one embodiment of the invention, proteins are further removed from the substrate prior to the initiation of fermentation. Proteins can be removed according to methods known in the state of the art, a precipitation of proteins by cooling the substrate is particularly preferred. The precipitated proteins can subsequently be separated and dried.

In this manner, a substrate with a high content of starch and a low content of solids of 3 to 15%, and preferably with a content of solid matter of 6 to 10%, can be obtained. The determination of the solid content is performed by centrifugation. Due to the substrate's low content of solids, it is possible to perform a particularly advantageous separation process after distillation.

During fermentation, the carbohydrates present in the biomass are fermented by the addition of microorganisms, thereby producing alcohols, in particular large amounts of ethanol. Usually, yeasts are added for the initiation of fermentation. The fermentation is usually carried out according to methods known in the state of the art. Preferably, yeasts are used for fermentation and the fermentation stops, when substantially all carbohydrates have been transformed by fermentation.

Preferably, the yeast S. cerevisiae is used for fermentation. In the method of the invention, fermentation can be carried out in a batch process, a cascading process or in a continuous process with reuse of yeast.

An alcoholic mash is obtained by fermentation. The alcohol present in the mash can be distilled and further purified by methods known in the state of the art. The known methods for distillation, rectification and dehydration can be employed. By the separation of bran and, if applicable, the proteins, according to the invention, less side-products of ethanol are generated during fermentation. This leads to a high-quality crude alcohol, which reduces the expense for rectification. The efficiency of the process according to the invention is thus improved by the use of the alcoholic mash having a lower content of solids.

Preferably, the crude ethanol obtained by distillation is rectified and, if necessary, dehydrated, in order to obtain bioethanolor neutral ethanol.

As a further product of the distillation, a pulp is obtained. As this is pulp from the production of alcohol, the pulp can also be referred to as alcoholic pulp.

According to the process of the invention, the pulp obtained by distillation can subsequently be cooled and divided into a solid phase and a clear phase. After distillation, the pulp has a temperature of approximately 100° C. and a milky color. After cooling, the pulp has a temperature of approximately 30 to 40° C. and contains solid matter which precipitated during cooling. This solid matter can be separated according to the invention, for example by use of a separator, preferably a disk separator.

In the method for separating the solid phase and clear phase of the pulp, a decanter or a disk centrifuge is preferably employed. It is energetically more efficient to use the decanter, which is therefore preferred. Preferably, about 80% of the liquid in the pulp is withdrawn as a clear phase.

The clear phase has a content of solids of less than 10%, preferably clearly less than 10%, such as less than 5% or 1%, wherein obtaining a clear phase with a content of solids of less than 0,5% is particularly preferred. The content of solids refers, if not otherwise mentioned, to volume percentages, and can easily be determined by sedimentation. Alternatively, a centrifugation for separating solid and liquid components can be carried out, allowing an indication of the content of solids in weight percentages.

The clear phase can be used for obtaining methane in the process of the invention. The use of a clear phase with a lower content of solid matter in this step of the procedure has the particular advantage that methanation of the clear phase of the pulp can be performed in a so-called high-performance reactor. An respective reactor works with beads which usually have a diameter of 1 to 2 mm and in which methane bacteria are immobilized. Thereby, a multiple, preferably at least a 5-fold space time yield can be obtained. Usually, the beads are sponge-like and consist of lime. By use of these beads, the efficiency of the reactor is considerably increased compared to conventional reactors. The use of these reactors for the first time renders possible the construction of a particularly advantageous bioethanol plant, which comprises methanation of the pulp and has a very high daily capacity, in particular a daily capacity of more than 100, 300, preferably more than 500 $m^3$ ethanol per day.

A particularly preferred embodiment of the invention therefore is a method for producing ethanol and methane from grain, comprising
a) milling the grain to a particle size of less than 0,6 mm and separating bran and hull components from the flour;
b) enzymatically liquefying and sacchariyfing the flour in a conventional manner in the presence of water, thereby obtaining a mash;
c) fermenting and distilling the substrate in a conventional manner, thereby obtaining ethanol and pulp;
d) agglomerating yeast, fibers, solid substances, fat and/or proteins present in the pulp by cooling and sedimenting them;
e) dividing the pulp into a solid phase and a clear phase, wherein a clear phase with a content of solids of less than 1% is obtained; and
f) obtaining methane from the clear phase in a high performance methane reactor.

Preferably, a high-performance methane reactor is employed wherein the immobilisation of the methane bacteria in the beads increases the space time yield in the reactor. Preferably, a space time yield of at least 5 to 25, preferably at least 10, at least 12 or most preferably at least 25 kg CSB/ ($m^3$*d) is allowed. In conventional reactors, space time yields of ca. 5 kg CSB/($m^3$*d) are generally reached.

Preferably, a high-performance methane reactor allowing preacidification/conditioning is employed.

The reactor can be preceded by a mixing and compensation vessel which allows a qualitatively and quantitatively constant supply of clear phase to the methanation plant. By circulation pumps, an intensive fluid exchange between the two vessels is achieved.

In the lower part and the middle part of the reactor, the methane bacteria beads can be kept suspended by the ascending gas and additional pumping. In this manner an intensive mixing of the reaction material is achieved, which further increases the efficiency. Preferably, collectors are located in the upper part of the reactor, which retain the immobilized methane bacteria lime beads in the reactor.

The content of solids present in the substrate is entrained by the liquid flow; after deposition they leave the system together with the purified substrate. If a higher content of solids is used, the solids will accumulate in the methane reactor, thus leading to a stop of agitation of the immobilized methane bacteria and a stop of the entire process. Extensive studies with a technical plant have shown that the process can be carried out with particular advantages in this step, when the content of solids of the clear phase of the pulp is 0,5% or less.

Figure 1:
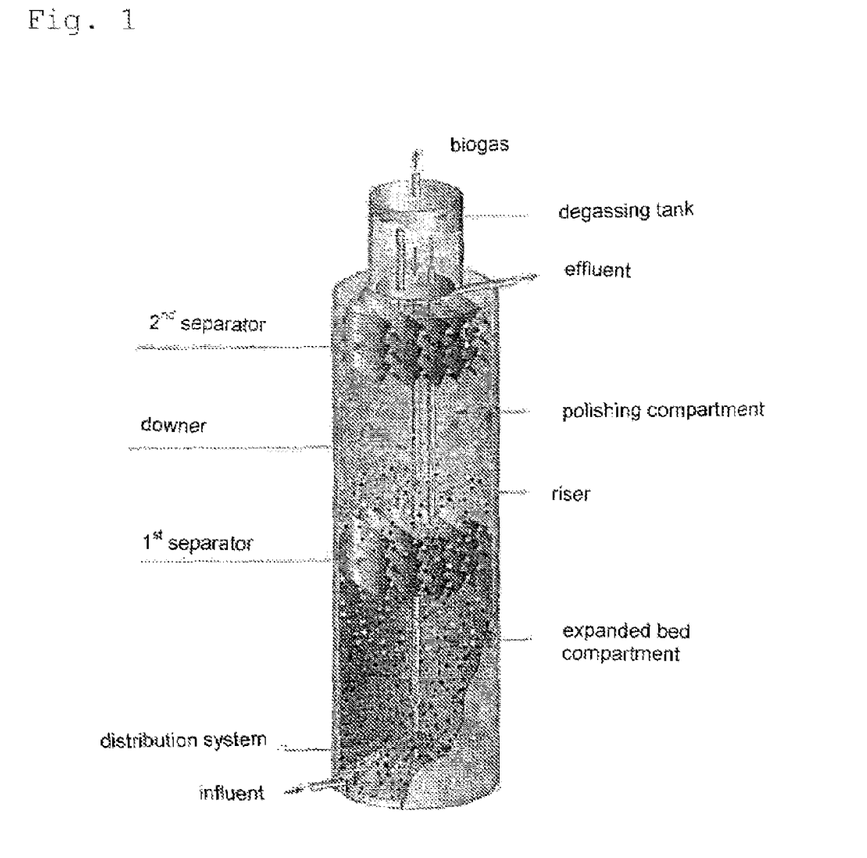
FIG. 1 shows the scheme of a high performance reactor used in the invention witch is based on the principle of IC (Internal Circulation).

In particular, in the method of the invention, a high-performance methane reactor comprising an Upflow anaerobic sludge blanket (UASB)-reactor is employed. It is particularly preferred to employ a further development of this technique, an Internal Circulation (IC)-Reactor. With an IC-Reactor, e.g. from the company PAQUES, Netherlands, space time yields of ca. 30-35 kg CSB/(m3*d) can be reached. A scheme of such a reactor with the characteristic fixtures for three phase separation (liquid, gas, pellets/beads of microorganisms) is shown in FIG. 1. Other reactor types, such as low performance stirred tank reactors, reactors working with conventional activated sludge processes with or without sedimentation and recycling of substrate, and fixed bed reactors are not suitable for large-scale use in production of bioethanol due to the necessary long retention times.

The methane can subsequently be converted to energy or heat according to methods known in the art, whereby energy and process heat are generated which cover the energy need of the conversion.

Particularly preferred is a combination of the method of the invention with an especially efficient waste water treatment that allows recycling of the water into the process, e.g., for liquefying the flour, or direct dumping of the water. The invention therefore also relates to a method wherein the clear phase of the pulp is purified aerobically after anaerobic purification in the methane reactor.

An efficient anaerobic and aerobic purification of the clear phase also makes it possible to add the anaerobically/aerobically purified clear phase to the conversion process as water for dilution. Preferably, this does not affect the quality of the crude ethanol.

Preferably, anaerobically/aerobically purified clear phase is employed for the addition of water for liquefaction of the flour, a method wherein the water needed for liquefaction of the flour is completely supplied by anaerobically/aerobically purified clear phase.

Thereby, the method of the invention also allows a large-scale bioethanol production by significantly reducing the required amount of fresh water, by reducing the amount of waste water and enhancing the quality of waste water.

The solid phase of the pulp, also called thick phase, can also be profitably processed. In one embodiment of the invention, the solid phase of the pulp is processed for producing a feedstuff (Distilled Dried Grain Solution, DDGS) and/or fertilizer.

Preferably, the solid phase of the pulp is mixed with separated hull components and/or bran. Furthermore, the separated proteins can also be mixed with the solid phase of the pulp. Preferably, the mixture is further dried, e.g. with a tube bundle dryer. Upon mixing with the bran, the content of solids of the dried material is usually increased so much that a laborious recycling that otherwise light be necessary can be dispensed with. The obtained vapour can be joined with the clear phase and applied to methane production.

The solid phase of the pulp can be mixed with the solid phases previously obtained, namely with the proteins and the bran. It is preferred that the mixture obtained in this manner is subsequently dried under mild temperatures. Thereby a feeding stuff is obtained which has a higher quality compared to feeding stuffs obtained by methods for the production of alcohol from biomass known in the art.

Another embodiment of the present invention is a method for producing energy and/or heat, comprising the method of the invention for producing ethanol and methane and converting the methane to energy and/or heat. The energy yield of the method can be consequently improved by dispensing with the production of feedstuff or fertilizer and drying and burning the solid phase of the pulp for the generation of energy. Preferably, an energy yield (energy output/energy input) positive over the whole process is reached. Drying can be carried out with convenient, simple methods, as the quality as feedstuff is not relevant for burning. Burning the solid phase is especially preferred upon use of rye as biomass, as feedstuff produced from rye is not easily digestible.

Therefore, the invention also relates to a method for producing energy and/or heat, comprising a method for producing ethanol and methane from grain, comprising
 a) milling the grain to a particle size of less than 1 mm, preferably less than 0,6 mm and separating bran and hull components from the flour;
 b) enzymatically liquefying and sacchariyfing the flour in a conventional manner in the presence of water, thereby obtaining a mash;
 c) fermenting and distilling the substrate in a conventional manner thereby obtaining ethanol and pulp;
 d) agglomerating yeast, fiber, solid substances, fat and/or proteins by cooling and sedimenting them;
 e) dividing the pulp into a solid phase and a clear phase, wherein a clear phase with a content of solids of less than 1% is obtained; and
 f) obtaining methane from the clear phase in a high-performance methane reactor and drying and burning the solid phase of the pulp under generation of energy.

The invention further relates to the use of the clear phase of pulp from the production of bioethanol with a content of solids of less than 10%, preferably less than 5% or 1% and especially preferred less than 0,5% (w/v) for producing methane, energy and/or heat. Preferably, a high-performance methane reactor is used therefor, in particular one of the high performance reactors described above.

In a further aspect, the present invention provides production plants for producing ethanol and methane from a biomass in accordance with any of the methods outlined above. The production plant comprises a means for fermentation, distillation, and a high-performance methane reactor.

The present invention also provides ethanol, methane and/or energy obtainable according to any of the methods described above.

FIG. 1.

FIG. 2:
 A preferred process according to the invention is shown in FIG. 2.

Figure 2:
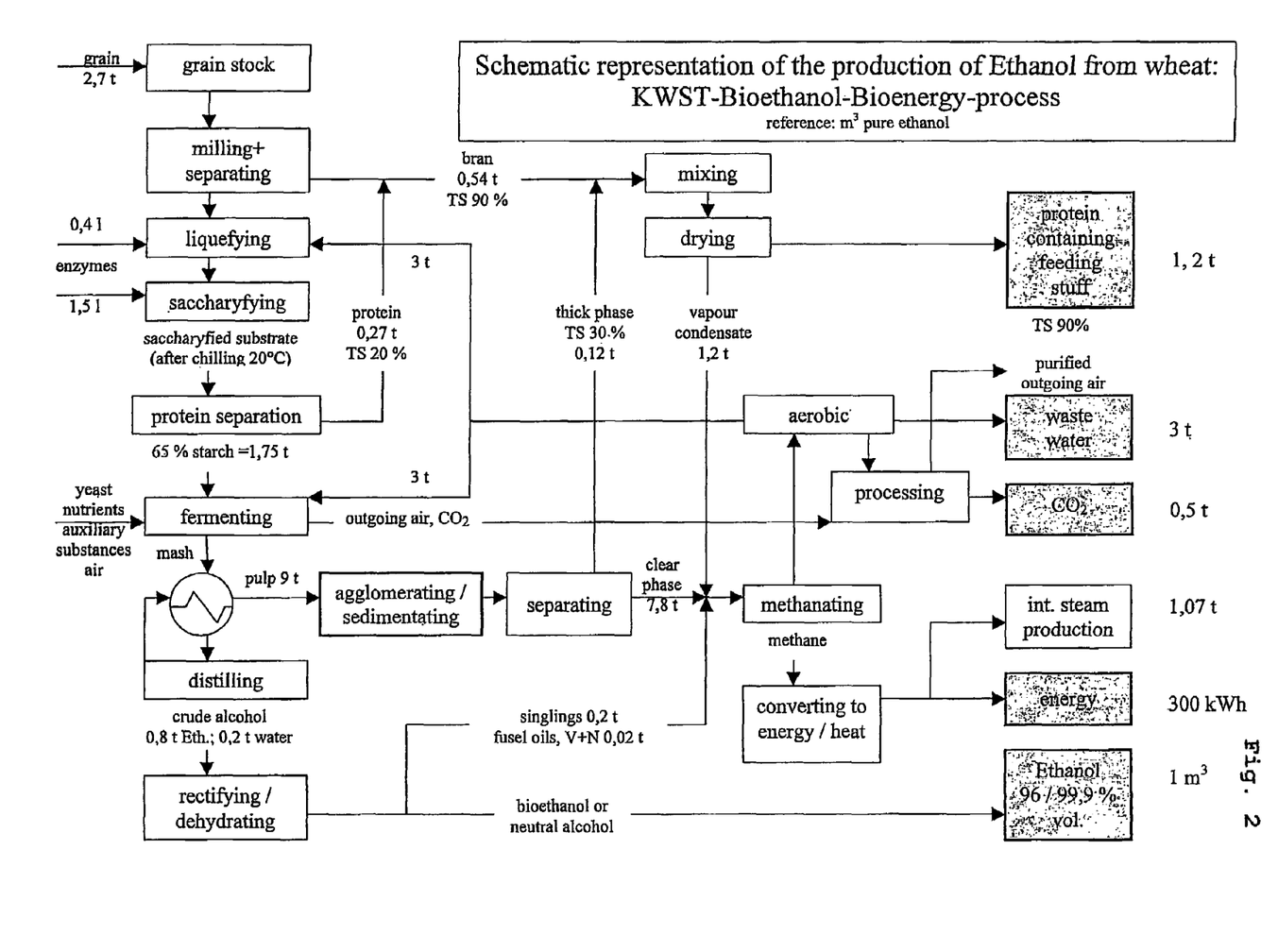
FIG. 2 illustrates the process according to the invention as presently conducted in an experimental production plant. However, it should be understood from the above description that not all steps which are illustrated in FIG. 2 are necessary for obtaining the advantages of the invention.

As shown in FIG. 2, grain from a grain stock is provided. Subsequently, the grain is milled and the bran is separated.

By the addition of enzymes, auxiliary substances and water, the grain is liquefied and subsequently saccharified. The proteins present in the saccharified substrate are precipitated by cooling and separated. A substrate is obtained which comprises all of the starch in the grain. In this manner, the components which do not produce alcohol are separated prior to the fermentation process.

This substrate serves as a medium for fermentation. For this purpose, yeast, nutrients, such as ammonium sulfate and bitter salt, air and water are added.

The fermentation produces an alcoholic mash which is employed in a distillation for the production of a crude alcohol according to methods known in the art. In the distillation, crude alcohol is produced which is purified by rectification and dehydration to bioethanol or a neutral alcohol. The purity of the product obtained can be between 96 and 99,9 vol-%. If fusel oils, singlings, pre- and last runnings are produced during this procedure, these can be used for the production of methane.

As a side-product of the distillation, pulp is obtained, which is first cooled and subsequently divided into a solid phase and a liquid phase. The liquid phase is introduced into the methanation production plant. The methane obtained is converted to energy, and process heat is obtained.

The solid phase obtained from the separation of the pulp is mixed with the bran and the proteins and subsequently dried. Thereby, a protein-containing feeding stuff is obtained which is suitable for feeding animals, in particular cows, pigs, horses, etc.

FIG. 3:

EXAMPLES

1) Energy Balance

A trial plant, which corresponds to the system depicted in FIG. 2, has been run for months and has been used batch-wise for the production of ethanol, wherein 100 l ethanol were obtained from 170 kg starch. Based on these studies, the following energy balance was obtained for the process according to the invention:

1. Quantity balance

Mash containing approximately 10 vol-% ethanol. Therefore, the following quantity balance applies for the mash:

| mash: 10 vol-% ethanol | 10 m$^3$/m$^3$ ethanol |
|---|---|
| ethanol (pure) | 1 m$^3$/m$^3$ ethanol |
| pulp | 9 m$^3$/m$^3$ ethanol |

2. Energy content of the clear phase of the pulp suitable for methanation:

2.1 Content of the clear phase:

In this section, the chemical oxygen demand (COD) per m$^3$ ethanol of the clear phase of the pulp according to the invention is described and the portion which is available for energy production by methanation:

| burden per m$^3$ waste water | 40 kg COD/m$^3$ |
|---|---|
| biotechnical availability | 80% |
| net burden per m$^3$ waste water | 32 kg COD/m$^3$ |

The clear phase thus provides carbohydrates for methanation which have a chemical oxygen demand of 32 kg/m$^3$ waste water.

The clear phase has an energy content of 100 kWh/m$^3$ waste water.

2.2 From the above, the following energy balance can be inferred in relation to ethanol:

Pulp (normative)=9 m$^3$ pulp/m$^3$ ethanol×energy content=900 kWh/m$^3$ ethanol.

Corresponds to 3600 MJ/m$^3$ ethanol.

3. In comparison, the process of the invention has an energy requirement which is as follows:

3.1 Energy consumption distillation/rectification:

steam requirement: 1800 kg/m$^3$ ethanol×2,02 MJ/kg=3636 MJ/m$^3$ ethanol (estimated);

energy requirement: 302 kWh/m$^3$×3,6 MJ/kg=1087 MJ/m$^3$ ethanol; and total energy consumption=4723 MJ/m$^3$ ethanol.

3.2 Energy consumption of drying the pulp:

steam requirement: 1250 kg/m$^3$ ethanol×2,02 MJ/kg=2525 MJ/m$^3$ ethanol;

energy requirement: 50 kWh/m$^3$ ethanol×3,6 MJ/kg=180 MJ/m$^3$ ethanol;

Drying the pulp therefore consumes energy corresponding to a total of 2705 MJ/m$^3$ ethanol.

3.3 Therefore, the total energy consumption (3.1 and 3.2) is:

steam requirement of 3050 kg/m$^3$ ethanol×2,02 MJ/kg=6161 MJ/m$^3$ ethanol; and energy requirement of 352 kWh/m$^3$ ethanol×3,6 MJ/kg=1267 MJ/m$^3$;

The total energy consumption therefore is 7428 MJ/m$^3$ ethanol.

4. In contrast, the energy balance of conventional methods is:

steam requirement for the distillation/rectification, dehydration: 2200 kg/m$^3$ ethanol×2,02 MJ/kg=4400 MJ/m$^3$ ethanol;

energy requirement for the distillation/rectification, dehydration: 302 kWh/m$^3$ ethanol×3,6 MJ/kg=1087 MJ/m$^3$ ethanol;

steam requirement for drying the grain pulp: 3100 kg/m$^3$ ethanol×2,02 MJ/kg=6262 MJ/m$^3$ ethanol;

energy requirement for drying the grain pulp: 178 kWh/m$^3$ ethanol×3,6 MJ/kWh=641 MJ/m$^3$ ethanol;

This corresponds to a total energy consumption of 12434 MJ/m$^3$ ethanol.

5. It was thus shown that the process according to the invention consumes 5006 MJ/m$^3$ ethanol less energy than the methods known in the art. This corresponds to a reduction of the energy consumption of 40%.

Further, if the energy production by methanation is added (3600 MJ/m$^3$ ethanol), an improvement of the energy balance of a total of 69% is obtained. In other words, the process according to the invention requires only approximately 30% of the energy which is required for carrying out conventional methods for the production of ethanol from biomass. This impressively demonstrates the advantages of the process according to the invention.

2) Energy Balance of an Improved Method

Figure 3:
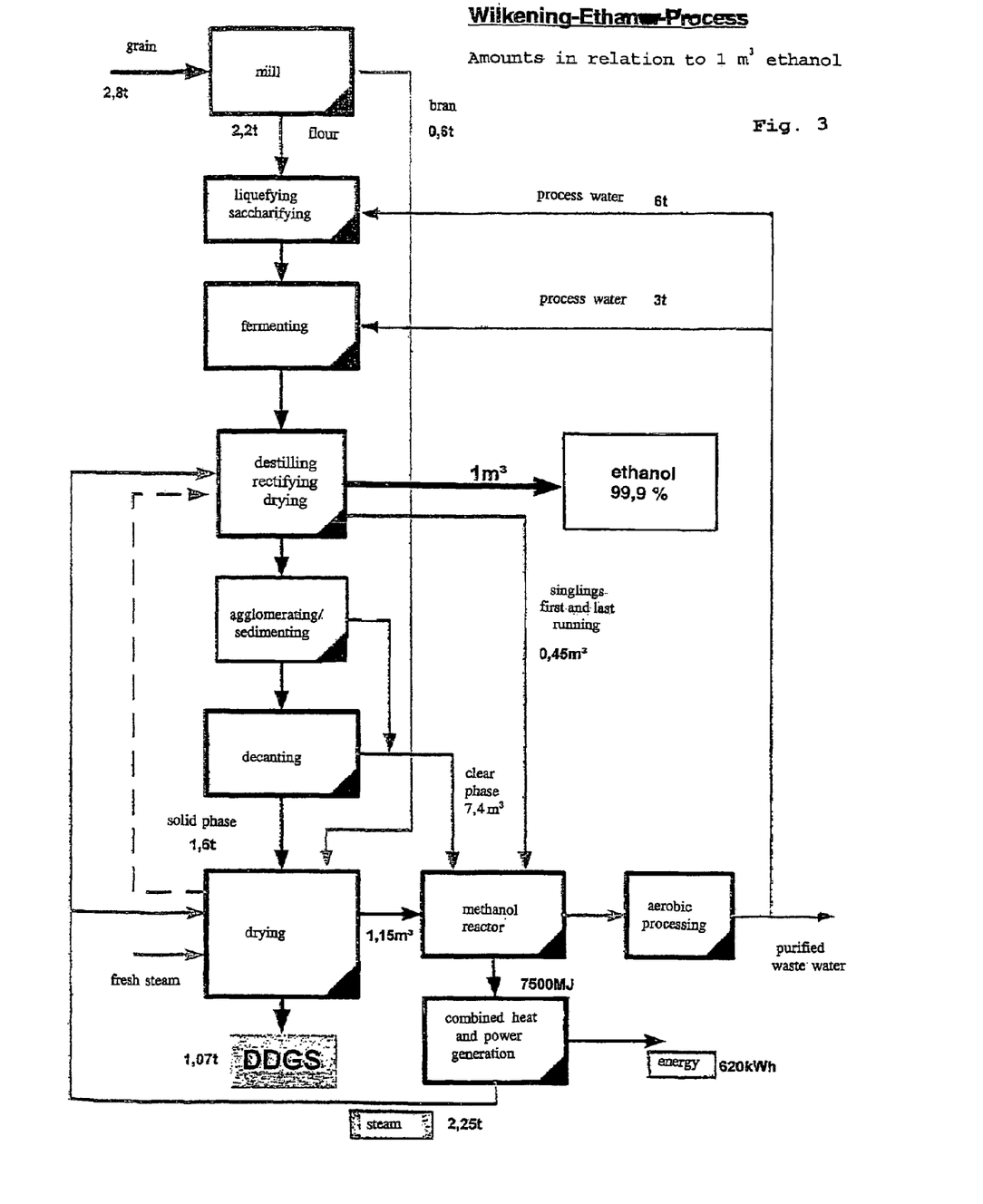
FIG. 3 shows a scheme of the process in a different preferred embodiment of the invention, wherein the separation of protein together with yeast, fat, fibres and solid components is carried out after fermentation and distillation by agglomeration and sedimentation.

The energy balance was improved by modifications of the method of the invention. The following energy balance relates to the method shown in FIG. 3. The amounts relate to a method, wherein 100 ethanol were obtained from 170 kg starch. Based on these studies, the following energy balance was obtained for the process according to the invention:

1. Quantity balance

Mash containing approximately 10 vol-% ethanol. Therefore, the following quantity balance applies for the mash:

| | |
|---|---|
| mash: 10 vol-% ethanol | 10 m³/m³ ethanol |
| ethanol (pure) | 1 m³/m³ ethanol |
| pulp | 9 m³/m³ ethanol |

2. Energy content of the clear phase of the pulp suitable for methanation:
2.1 Content of the clear phase:

In this section, the chemical oxygen demand (COD) per m³ ethanol of the clear phase of the pulp according to the invention is described and the portion which is available for energy production by methanation:

| | |
|---|---|
| burden per m³ waste water | 65 kg COD/m³ |
| biotechnical availability | 80% |
| net burden per m³ waste water | 52 kg COD/m³ |

The clear phase thus provides carbohydrates for methanation which have a chemical oxygen demand of 52 kg/m³ waste water.

2.2 From the above, the following energy balance can be inferred in relation to ethanol:

Pulp (normative)=9 m³ pulp/m³ ethanol×energy content corresponds to 7500 MJ/m³ ethanol.

3. In comparison, the process of the invention has an energy requirement which is as follows:

3.1 Energy consumption distillation/rectification/dehydration and drying:

steam requirement: 2240 kg/m³ ethanol×2,02 MJ/kg=4525 MJ/m³ ethanol (estimated);

energy requirement: 230 kWh/m³×3,6 MJ/kg=828 MJ/m³ ethanol; and total energy consumption=5353 MJ/m³ ethanol.

3.2 Methanisation of the clear phase and use in block type

| | | |
|---|---|---|
| thermal power station | | 7500 MJ/m³ Ethanol |
| loss | 10% | 753 MJ/m³ Ethanol |
| generation of energy | 30% | 2260 MJ/m³ Ethanol |
| generation of steam | 60% | 4520 MJ/m³ Ethanol |
| total energy yield | | 6780 MJ/m³ Ethanol |
| Energy surplus | 32% | 1427 MJ/m³ Ethanol |

3.3
4. In contrast, the energy input of known methods is:
4.1 Vogelbusch-method

| steam | energy | total |
|---|---|---|
| 3.5 t/m³ Ethanol | 360 kWh/m³ Ethanol | |
| 7 070 MJ/m³ Ethanol | 1296 MJ/m³ Ethanol | 8366 MJ/m³ Ethanol |

4.2 Jaakko Pöyry

| steam | energy | total |
|---|---|---|
| 3.43 t/m³ Ethanol | 366 kWh/m³ Ethanol | |
| 6929 MJ/m³ Ethanol | 1318 MJ/m³ Ethanol | 8247 MJ/m³ Ethanol |

5. It was thus shown that the process according to the invention consumes 5006 MJ/m³ ethanol less energy than the methods known in the art. This corresponds to a reduction of the energy consumption of 36%.

Further, if the energy production by methanation is added (6780 MJ/m³ ethanol), an improvement of the energy balance of a total of 82% is obtained.

3) Experimental Results from Production of Bioethanol

1. Methods 1.1 Disintegration

The experiments were carried out in a 1,2 m² stirred tank reactor with constant stirring at 300 rpm.

The preparation was formulated based on the recommendations of the supplier of enzyme, however, usually, with the double stoichiometrically necessary amount of enzyme. Enzymes of the company Gammazym were employed (alpha- and beta amylases, additionally, if required, cellulases). Liquefaction and saccharyfication were initiated by indirect warming. The prescribed temperature regimen was complied with (maximum temperature 85° C.). Saccharyfication temperature 65° C., pH 5, set original gravity 18,0 Bé.

Partly, anaerobically or anaerobically/aerobically purified clear phase of previous experiments was used as process water.

1.2 Fermentation

Brewer's dried yeast T01 of the company Gammazym of another dried yeast (AB Strand, Sweden) was employed. Fermentation temperature constantly was between ca. 25 to 35° C.

1.3 Distillation

The mash was completely indirectly distilled by charging the trial reactor with steam and bringing it to the boil (pot distillation). The maximum ethanol content reached was ca. 60% v/v. The quality of the crude ethanol was controlled by gas chromatography.

1.4 Processing of Pulp

The pulp was separated prior to further processing. The pulp, milky without visible solid components, was cooled to 30° C. The pulp flocculated during this process. A spinning test yielded a solid phase and a clear liquid phase. At the beginning, an automatically emptying disk centrifuge WSPX 303 of the company Alfa-Laval was employed, later a decanter type 1600 of the company Alfa-Laval. The content of solids in the clear phase of the pulp was determined by sedimentation.

1.5 Methanisation

Methanisation of the clear phase of the pulp was carried out in a BIOPAQ® experimental reactor of the company PAQUES, Netherlands, according to the producer's specification. The experimental plant consists in a 60 l IC-reactor and a 35 l preacidification/conditioning, and it is equipped with pumps, temperature control, pH control and a device for measuring flow of gas. The plan is fully automated. The results obtained with this plant can essentially be transferred to bigger plants.

2. Results
2.1 Production of bioethanol

No Problems arose in the experiments with different raw materials (flour of wheat and rye of different particle size, starch). Sometimes, the viscosity increased significantly upon dosed mashing of flour in cold water, therefore, a part of the cellulase "Gammaclast" was already added at this time point. The further conventional addition of enzymes reliably prevented agglutination of the substrate upon warming. The amount stoichiometrically necessary was generally doubled. Addition of saccharifying enzyme was also increased to guarantee completeness of the enzymatic processes.

Culture of yeast in the fermenter was always successful, a clean, uniform pattern of yeast could be seen microscopically, the concentration of yeast was very good.

The generation of ethanol is shown on the basis of an example (wheat flour). Measurements were made at the following times:
after 15 h: 8,3% v/v
after 40 h: 11,7% v/v
after 64 h: 13,6% v/v The final content of ethanol (measured after 150 h) was 13,6% (v/v) with an residual content of glucose of 27 g/l (enzymatical determination of glucose), the glucose was thus not totally broken down.

According to the amount of starch employed, the yield was 56 l pure Ethanol/100 kg starch, or 28 l pure Ethanol/100 kg raw material. The residual glucose concentration corresponds to ca. 18 l pure Ethanol, so the yield of ethanol related to the raw material is 61,7 l pure ethanol/100 kg starch or 30,5 l pure ethanol/100 kg raw material.

GC of the 60% (v/v) ethanol fraction obtained showed an excellent quality of crude ethanol.

2.2 Methanisation of the clear phase of the pulp

Success of the generation of methane from the clear phase of the pulp strongly depended on the raw material used for the generation of bioethanol, especially on the level of milling of the flour. With flour from wheat that was used at first, which was ground with swing-hammer mills and had a particle size of ca. 2 mm and a percentage of bran of ca. 10%, a methanisation of the clear phase of the pulp was not possible with the employed reactor. Feeding led to blocking and flushing out of the biomass. The content of solids of the clear phase of the pulp was ca. 6 to 15% in these experiments.

Different Experiments were carried out to reduce the content of solids and prevent agglomeration of the pellets of micro-organisms in the reactor.

Experiments of flour from wheat with different, defined grain size showed that this significantly affects the content of solids in the pulp. Only fine particles (less than 1 mm, preferably less than 0,6 mm or 0,2 mm particle size) led to a low content of solids in the decanted pulp allowing use of the reactor.

Positive results were obtained with starch that was essentially protein-free (0,35% protein) (content of solids in the clear phase 0,6% v/v), rye flour (content of solids in the clear phase 0,1-0,2% v/v) or wheat flour, e.g., WM550 (content of solids in the clear phase 0,1-0,5% v/v). The best results were obtained with wheat flour with a particle size of 0,2 mm when proteins were separated only after fermentation upon cooling the pulp.

No problems with the operation of the reactor arose upon use of clear phase with a content of solids below 1%. A space time yield of up to 20, sometimes up to 31 kg $CSB/(m^3*d)$ was reached and a good purification of water was possible.

2.3 Recycling of waste water

Experiments for the use of the clear phase of pulp as process water for mashing the flour showed that the quality of crude ethanol clearly diminished (increased concentration of acetic acid), if water that had been anaerobically purified by methanisation, but not aerobically purified, was used. Using anaerobically/aerobically purified clear phase of the pulp, even up to 100%, no impairment of the quality of crude ethanol was noted.

The invention claimed is:

1. A method for producing ethanol and methane from a grain, comprising:
    a) obtaining a mash in the presence of water by enzymatically liquefying and saccharifying flour of said grain, wherein said flour has a particle size of less than 1 mm;
    b) obtaining ethanol and a pulp from said mash by fermenting and distilling;
    c) separating the pulp into a solid phase and a clear phase, wherein said clear phase comprises solids of less than 1%; and
    d) obtaining methane from said clear phase in a high-performance methane reactor.

2. The method according to claim 1, further comprising milling grain to a particle size of less than 1 mm, thereby producing flour.

3. The method according to claim 1, wherein said grain comprises a hull component that is separated from flour prior to step a, or separated from said prior to step b.

4. The method according to claim 1, wherein said grain is selected from the group consisting of wheat, rye, maize and triticales.

5. The method according to claim 1, wherein said particle size of said flour is less than 0.6 mm.

6. The method according to claim 1, further comprising separating protein present in said grain from said flour prior to step a or separated from said mash prior to step b or separated from said clear phase of said pulp in step c.

7. The method according to claim 6, wherein said separating of said protein prior to step b comprises precipitation by cooling and separation of the precipitate.

8. The method according to claim 6, wherein the said separating of said proteins in step c comprises precipitation by cooling and separation of the precipitate.

9. The method according to claim 8, further comprising agglomerating yeast, fiber, solid substances, fat, protein, or combinations thereof present in said pulp prior to separation of said pulp into solid phase and clear phase.

10. A method for producing ethanol and methane from a grain, comprising
    a) obtaining a flour by milling said grain to a particle size of less than 1 mm and separating a bran and a hull component from said flour;
    b) obtaining a mash by enzymatically liquefying and saccharifying said flour in the presence of water;
    c) obtaining a protein and a substrate by precipitating said protein present in said mash, wherein said precipitating is accomplished by cooling, sieving and drying;
    d) obtaining ethanol and pulp from said substrate by fermenting and distilling;
    e) separating said pulp into a solid phase and a clear phase, wherein said clear phase comprises solids of less than 1%; and
    f) obtaining methane from said clear phase in a high-performance methane reactor.

11. The method according to claim 10, wherein said solid phase and said clear phase of the pulp are separated in a decanter or a disk centrifuge.

12. The method according to claim 10, wherein said clear phase comprises about 80% of the liquid from said pulp.

13. The method according to claim 10, wherein said clear phase comprises solids of less than 0.5%.

14. The method according to claim 10, wherein said fermenting is carried out in a batch process, in a cascading process, or in a continuous process comprising a recycling of yeast.

15. A method for producing ethanol and methane from a grain, comprising
   a) obtaining a flour by milling said grain to a particle size of less than 1 mm, and separating a bran and a hull component from a flour;
   b) obtaining a mash by enzymatically liquefying and saccharifying said flour in the presence of water;
   c) obtaining ethanol and a pulp from said mash by fermenting and distilling;
   d) agglomerating yeast, fiber, solid substances, fats, protein, or combinations thereof, present in said pulp by cooling and sedimenting;
   e) obtaining a solid phase and a clear phase from said pulp, wherein said clear phase comprises solids of less than 1%; and
   f) obtaining methane from said clear phase in a high-performance methane reactor.

16. The method according to claim 15, wherein said high-performance methane reactor comprises, beads with a diameter of 1 to 2 mm in which methane bacteria are immobilized.

17. The method according to claim 16, wherein said immobilized methane bacteria in said beads increases the space-time yield in said reactor and preferably allows a space-time yield of at least 25 kg CSB/(m$^3$*d).

18. The method according to claim 15, wherein said clear phase is pre-acidified and conditioned prior to said obtaining methane production in a high-performance methane reactor.

19. The method according to claim 15, wherein said high-performance methane reactor comprises an Upflow anaerobic sludge blanket (UASB)-reactor.

20. The method according to claim 15, wherein said high-performance methane reactor comprises an Internal Circulation (IC)-reactor.

21. The method according to claim 10, wherein said ethanol is rectified and, if necessary, dehydrated, in order to obtain bioethanol or neutral ethanol.

22. The method according to claim 1, wherein more than 100 m$^3$ ethanol/day are produced.

23. The method according to claim 1, wherein more than 300 m$^3$ ethanol/day are produced.

24. The method according to claim 1, further comprising processing said clear phase of said pulp aerobically or anaerobically after said obtaining methane from said clear phase in a high-performance methane reactor.

25. The method according to claim 24, wherein said anaerobically or aerobically purified clear phase is added to a conversion process as water for dilution.

26. The method according to claim 24, wherein said anaerobically or aerobically purified clear phase is employed for the addition of water for liquefaction of a flour.

27. The method according to claim 10, further comprising obtaining a mixture by mixing said solid phase of said pulp with said separated hull component, said bran, or a combination thereof.

28. The method according to claim 10, wherein said solid phase of said pulp is mixed with said precipitated protein to obtain a mixture.

29. The method according to claim 27, wherein said mixture is further dried.

30. The method for producing a feeding stuff, a fertilizer, or a combination thereof comprising a method for producing ethanol and methane from grain, comprising
   a) obtaining a flour by milling the grain to a particle size of less than 1 mm and separating the bran and hull components from the flour;
   b) obtaining a mash by enzymatically liquefying and saccharifying said flour in the presence of water;
   c) obtaining a protein and a substrate by precipitating the proteins, wherein said precipitating is performed by cooling, sieving and drying;
   d) obtaining ethanol and pulp from said substrate by fermenting and distilling;
   e) separating said pulp into a solid phase and a clear phase, wherein said clear phase comprises solids of less than 1%;
   f) obtaining methane from said clear phase in a high-performance methane reactor; and
wherein said solid phase is mixed with said separated hull components, bran, or combinations thereof to obtain a mixture.

31. A method for producing energy, heat, or a combination thereof, comprising a method for producing ethanol and methane from grain, comprising:
   a) obtaining a mash in the presence of water by enzymatically liquefying and saccharifying the flour of said grain wherein said flower has a particle size of less than 1 mm;
   b) obtaining ethanol and a pulp from said mash by fermenting and distilling;
   c) separating said pulp into a solid phase and a clear phase, wherein said clear phase comprises solids of less than 1%; and
   d) obtaining methane from said clear phase in a high-performance methane reactor wherein said methane is converted to energy, heat, or a combination thereof.

32. The method according to claim 15, wherein said solid phase of said pulp is dried and burned for the generation of energy.

33. The method for producing energy, heat, or a combination thereof comprising a method for producing ethanol and methane from grain, comprising
   a) obtaining a flour by milling said grain to a particle size of less than 0.6 mm and separating away bran and hull components from said flour;
   b) obtaining a mash by enzymatically liquefying and saccharifying said flour in the presence of water;
   c) obtaining ethanol and pulp by fermenting and distilling said mash;
   d) agglomerating yeast, fiber, solid substances, fat, protein, or combinations thereof by cooling and sedimenting them;
   e) separating said pulp into a solid phase and a clear phase, wherein said clear phase comprises solids of less than 1%;
   f) obtaining methane from said clear phase in a high-performance methane reactor; and
   g) generating energy by drying and burning said solid phase of said pulp.

34. A method of using a clear phase of a pulp from a production of bioethanol wherein said clear phase comprises solids of less than 1% (w/v), comprising employing a high-performance methane reactor, comprising a bead with a diameter of 1 to 2 mm in which methane bacteria are immobilized and producing methane, energy, heat, or combinations thereof.

35. The method according to claim 34, wherein said immobilized methane bacteria in said bead increases the space-time yield in the reactor and optionally allows a space-time yield of at least 25 kg CSB/(m$^3$*d).

36. The method according to claim 34, wherein the method of preparing methane in a high-performance methane reactor further comprising pre-acidification, conditioning, or a combination thereof.

37. The method according to claim 34, wherein said high-performance methane reactor comprises an Upflow anaerobic sludge blanket (UASB) reactor.

38. The method according to claim 34, wherein said high-performance methane reactor comprises an International Circulation (IC) reactor.

39. A production plant for producing ethanol and methane from a grain by:
  a) obtaining a mash in the presence of water by enzymatically liquefying and saccharifying the flour of said grain wherein said flower has a particle size of less than 1 mm;
  b) obtaining ethanol and a pulp from said mash by fermenting and distilling;
  c) separating said pulp into a solid phase and a clear phase, wherein said clear phase comprises solids of less than 1%; and
  d) obtaining methane from said clear phase in a high-performance methane reactor comprising a means for fermentation, a means for distillation, and a high-performance methane reactor.

40. The method of claim 15 wherein said particle size is less than 0.6 mm.

41. The method according to claim 9, wherein said agglomerating comprises cooling and sedimenting said pulp.

* * * * *